(12) United States Patent
Molinier et al.

(10) Patent No.: US 10,265,688 B2
(45) Date of Patent: Apr. 23, 2019

(54) METHOD AND CATALYST SYSTEM FOR IMPROVING BENZENE PURITY IN A XYLENES ISOMERIZATION PROCESS

(71) Applicant: ExxonMobil Chemical Patents Inc., Baytown, TX (US)

(72) Inventors: Michel Molinier, Houston, TX (US); Hari Nair, Somerville, NJ (US); Xiaobo Zheng, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 106 days.

(21) Appl. No.: 15/222,197

(22) Filed: Jul. 28, 2016

(65) Prior Publication Data

US 2017/0081259 A1    Mar. 23, 2017

Related U.S. Application Data

(60) Provisional application No. 62/221,992, filed on Sep. 22, 2015.

(51) Int. Cl.
*B01J 29/44* (2006.01)
*C07C 5/27* (2006.01)
(Continued)

(52) U.S. Cl.
CPC ............... *B01J 29/44* (2013.01); *B01J 29/48* (2013.01); *B01J 35/0006* (2013.01);
(Continued)

(58) Field of Classification Search
CPC ..... C07C 15/08; C07C 5/2737; C07C 5/2775; C07C 2529/44; C07C 2529/48; B01J 2229/123; B01J 2229/186; B01J 2229/20; B01J 2229/32; B01J 2229/42; B01J 29/44; B01J 29/48; B01J 35/0006; B01J 35/023; B01J 35/006
See application file for complete search history.

(56) References Cited

U.S. PATENT DOCUMENTS 3,702,886 A    11/1972   Argauer et al.
3,709,979 A    1/1973    Chu
(Continued)

FOREIGN PATENT DOCUMENTS

WO    96/16004 A    5/1996

*Primary Examiner* — Sharon Pregler

(57) ABSTRACT

A process and catalyst system is disclosed for producing para-xylene from a $C_8$ hydrocarbon mixture comprising ethylbenzene and at least one xylene isomer other than para-xylene. The process modifies the conventional process by operating with a higher weight hourly space velocity, lower pressure and lower hydrogen partial pressure, which allows production of on-specification benzene product without penalty with respect to ethylbenzene conversion, para-xylene approach to equilibrium or xylene losses. The catalyst system comprises a first catalyst bed comprising a first zeolite having a constraint index from 1 to 12 and an average crystal size from 0.1 to 1 micron and a platinum hydrogenation component, and a second catalyst bed comprising a second zeolite having a constraint index ranging from 1 to 12 and an average crystal size of less than 0.1 micron and a rhenium hydrogenation component.

13 Claims, 1 Drawing Sheet

(51) Int. Cl.
 *B01J 35/00* (2006.01)
 *B01J 29/48* (2006.01)

(52) U.S. Cl.
 CPC .......... *C07C 5/2737* (2013.01); *C07C 5/2775* (2013.01); *B01J 2229/123* (2013.01); *B01J 2229/186* (2013.01); *B01J 2229/20* (2013.01); *B01J 2229/32* (2013.01); *B01J 2229/42* (2013.01); *C07C 2529/44* (2013.01); *C07C 2529/48* (2013.01); *Y02P 20/52* (2015.11)

(56) References Cited

U.S. PATENT DOCUMENTS

| | | |
|---|---|---|
| 3,832,449 A | 8/1974 | Rosinski et al. |
| 4,016,218 A | 4/1977 | Haag et al. |
| 4,016,245 A | 4/1977 | Plank et al. |
| 4,046,685 A | 9/1977 | Bray |
| 4,076,842 A | 2/1978 | Plank et al. |
| RE29,948 E | 3/1979 | Dwyer et al. |
| 4,397,827 A | 8/1983 | Chu |
| 4,417,780 A | 11/1983 | Knapp |
| 4,556,477 A | 12/1985 | Dwyer |
| 5,476,823 A | 12/1995 | Beck et al. |
| 6,028,238 A | 2/2000 | Beck et al. |
| 7,247,762 B2 * | 7/2007 | Stern ................ C07C 5/2724 585/481 |
| 7,271,118 B2 | 9/2007 | Raich et al. |
| 2005/0059847 A1 | 3/2005 | Stern |

* cited by examiner

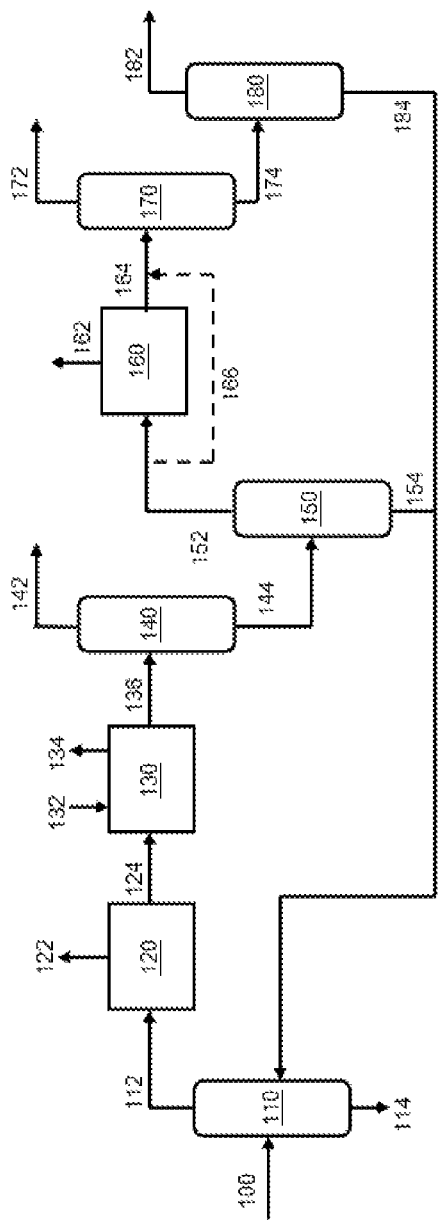

METHOD AND CATALYST SYSTEM FOR IMPROVING BENZENE PURITY IN A XYLENES ISOMERIZATION PROCESS

PRIORITY

This invention claims priority to and the benefit of U.S. Ser. No. 62/221,992 filed Sep. 22, 2015, which is herein incorporated by reference.

FIELD OF THE INVENTION

This invention relates to a process and catalyst system for improving benzene purity in a xylenes isomerization process.

BACKGROUND OF THE INVENTION

Para-xylene (PX) is a valuable chemical feedstock, which may be derived from mixtures of $C_8$ aromatics separated from such raw materials as petroleum naphthas, particularly reformates. The $C_8$ aromatic fractions from these sources vary quite widely in composition but will usually comprise 10 to 32 wt % ethylbenzene (EB) with the balance, xylenes, being divided between approximately 50 wt % of meta-xylene (MX) and 25 wt % each of para-xylene and ortho-xylene (OX). Of these isomers, para-xylene is by far the most important for commercial applications.

Individual isomer products may be separated from the naturally occurring $C_8$ aromatic mixtures by appropriate physical methods. Ethylbenzene may be separated by fractional distillation, although this is a costly operation. Ortho-xylene may be separated by fractional distillation, and is so produced commercially. Para-xylene may be separated from the mixed isomers by fractional crystallization, selective adsorption (e.g., the Parex™ or Eluxyl® process), or membrane separation.

As commercial use of para-xylene has increased, combining physical separation with chemical isomerization of the other xylene isomers to increase the yield of the desired para-isomer has become increasingly important. However, since the boiling point of ethylbenzene is very close to those of para-xylene and meta-xylene, complete removal of ethylbenzene from the $C_8$ aromatic feed by distillation is impractical. Hence an important feature of any commercial xylene isomerization process is the ability to convert ethylbenzene in the feed to useful by-products while simultaneously minimizing any conversion of xylenes to other compounds.

One xylene isomerization process that can effectively convert ethylbenzene is vapor phase isomerization, which is operated in a hydrogen-rich environment, in which a para-xylene-depleted $C_8$ aromatics stream, mostly composed of ethylbenzene, ortho-xylene and meta-xylene, undergoes two main transformations. First, ethylbenzene is dealkylated, yielding benzene and ethylene; this reaction is immediately followed by ethylene hydrogenation to ethane in order to avoid re-alkylation reactions involving ethylene. Second, ortho-xylene and meta-xylene are isomerized to equilibrium xylenes, meaning a xylene mixture comprising close to 24 mol % para-xylene.

A typical process for para-xylene production, known as a xylenes loop, will be to described with reference to FIG. 1. A $C_{8+}$ aromatics stream 100, for example, a reformate splitter bottoms stream, is provided to a xylenes column 110, where a $C_8$ aromatics stream 112 is separated from a $C_{9+}$ stream 114. The $C_8$ aromatics stream 112 is provided to a para-xylene recovery unit 120, where para-xylene is selectively removed to yield a high purity para-xylene product 122. The para-xylene depleted effluent 124, rich in ortho-xylene, meta-xylene and ethylbenzene, is sent to a vapor phase xylenes isomerization unit 130. The isomerization effluent 136 is provided to a deheptanizer column 150, in which a $C_{7-}$ aromatics stream 152 is separated from a $C_{8+}$ stream 154. The $C_{7-}$ aromatics stream 152 is fed to an extraction unit 160 and the $C_{8+}$ aromatics stream 154, in which the para-xylene mol % of total xylenes is approximately 24%, is recirculated to the xylenes column 110.

The vapor phase xylenes isomerization process produces a small amount of toluene, as the result of undesirable transalkylation reactions catalyzed by the active sites of the catalyst. This toluene is typically used in a toluene disproportionation, transalkylation unit or toluene methylation process to produce more para-xylene.

The vapor phase isomerization process also produces benzene as the result of the ethylbenzene dealkylation reaction. The amount of benzene product is directly proportional to the amount of ethylbenzene in the feed. The benzene produced is typically sold as a product, requiring a sufficient purity (99.85 wt % to 99.90 wt % or higher). However, because some vapor phase isomerization catalysts produce benzene co-boilers, the $C_{7-}$ aromatics stream 152 (containing benzene and toluene) from the deheptanizer column 150 must be processed in an extraction unit, extractive distillation or liquid-liquid extraction, to obtain adequate purity for the benzene to be sold as a product. The extraction unit 160 removes a non-aromatic stream 162, containing the benzene co-boilers, to produce a benzene/toluene-containing stream 164, from which a benzene stream 172 is removed in a benzene column 170. The toluene-containing stream 174 is sent to a toluene column 180 to produce a toluene stream 182 and a heavier aromatics stream 184 that is recycled to the xylenes column 110.

However, because extraction is a very energy intensive process, and also because in some cases the extraction unit is operating at full capacity, it is desirable to provide a process and/or catalyst system that minimizes the amount of benzene co-boilers produced, allowing production of a high purity benzene product with the bypass of the extraction unit.

SUMMARY OF THE INVENTION

The present invention is directed to a process and catalyst system for the isomerization of a para-xylene depleted stream that produces a high purity benzene product to without the need for extraction of the benzene stream.

In one embodiment, a process is provided that modifies the conventional process by operating with a higher weight hourly space velocity, lower pressure and lower hydrogen partial pressure, which allows production of on-specification benzene product without penalty with respect to ethylbenzene conversion, para-xylene approach to equilibrium or xylene losses. Thus, in the inventive process, a $C_{8+}$ hydrocarbon stream is provided to a para-xylene recovery unit, which produces a para-xylene rich stream and a para-xylene depleted stream. The para-xylene depleted stream is passed to a vapor phase isomerization unit to produce an isomerized stream. The vapor phase isomerization is conducted under conditions of about 175-180 psig, a hydrogen partial pressure of about 100-110 psia, and a weight hourly space velocity of about 15 hr$^{-1}$. The isomerized stream is sent to a deheptanizer column to separate a $C_{7-}$ aromatics stream from a $C_{8+}$ aromatics stream. The $C_{8+}$ stream is recycled back to said para-xylene recovery unit and the $C_{7-}$ aromatics stream is sent to a benzene column to recover a benzene stream, without being processed through an extraction unit. Any commercially known catalyst may be used in this process.

In another embodiment, a catalyst system is provided for isomerizing a para-xylene-depleted $C_8$ hydrocarbon mixture containing ethylbenzene to produce para-xylene and benzene that does not need to be extracted to achieve sufficient purity to be sold as a product. The catalyst system comprises two beds, the first of which comprises a first catalyst comprising a first zeolite having a constraint index ranging from 1 to 12 and an average crystal size of at least 1 micron, and a platinum hydrogenation component. The second catalyst bed comprises a second catalyst comprising a second zeolite having a constraint index ranging from 1 to 12 and an average crystal size of about 0.02-0.05 microns, and a rhenium hydrogenation component. A process using said catalyst is also provided.

BRIEF DESCRIPTION OF THE DRAWINGS

FIG. 1 is a schematic representation of a xylenes loop process.

DETAILED DESCRIPTION OF THE INVENTION

The present invention is directed to a process and catalyst system for the isomerization of a para-xylene depleted stream that produces a high purity benzene product without the need for extraction of the benzene stream.

Process

The overall process of the present invention follows the same steps as the conventional process described above. With reference to FIG. 1, a $C_{8+}$ aromatics stream 100, for example, a reformate splitter bottoms stream, is provided to a xylenes column 110, where a $C_8$ aromatics stream 112 is separated from a $C_{9+}$ stream 114. The $C_8$ aromatics stream 112 is provided to a para-xylene recovery unit 120, where para-xylene is selectively removed to yield a high purity para-xylene product 122. The para-xylene recovery unit 120 may be an adsorptive separation unit, crystallization unit, or a combination thereof, as known in the art. The para-xylene depleted effluent 124, rich in ortho-xylene, meta-xylene and ethylbenzene, is sent to a vapor phase xylenes isomerization unit 130, which is also provided with hydrogen 132 and from which a purge stream 136 is removed.

The inventive process allows for use of any commercially available high activity vapor phase isomerization catalyst. By high activity catalyst, it is meant that the catalyst achieves high ethylbenzene conversion, up to 75-90% conversion per pass, resulting in low ethylbenzene recirculation in the xylenes loop, translating to lower energy consumption and enhanced capacity in the para-xylene recovery unit. However, with a high activity catalyst, undesirable side reactions also occur at a higher rate, including ring saturation leading to benzene co-boilers, meaning the resultant benzene purity is insufficient to bypass the extraction unit. In one embodiment, the commercial catalyst system used for vapor phase isomerization is that described in U.S. Pat. No. 7,271,118, the entire contents of which are incorporated herein by reference.

The inventive process modifies the typical process conditions used to yield high purity benzene while operating at high ethylbenzene conversion. In a typical vapor phase isomerization process, the process is operated at a temperature of about 350° C. to about 450° C., a pressure of about 200 psig to about 400 psig, a hydrogen partial pressure of about 110 psia to about 220 psia, and a weight hourly space velocity (WHSV) of about 8 hr$^{-1}$ to about 12 hr$^{-1}$, achieving an ethylbenzene conversion (EBC) of about 50% to about 80%, with xylene losses of about 1.5-2.5%, a para-xylene approach to equilibrium (PXAE) greater than 100%, and a benzene purity of about 98.5-99.5 wt %. However, by operating with a higher WHSV, lower pressure and lower hydrogen partial pressure, on-specification benzene product can be obtained without penalty with respect to EB conversion, PXAE or xylene losses. These results are surprising because it is expected that higher benzene purity would be achieved by operating at higher severity, with a significant penalty in terms of increased xylene losses, which annul the benefits of higher benzene product purity, but the inventive process achieves higher benzene purity without the expected attendant xylene losses.

Operating the vapor phase isomerization unit 160 at a pressure of about 150-220 psig, a hydrogen partial pressure of about 80-110 psia, and a WHSV of about 14-18 hr$^{-1}$ to allows for the production of benzene with sufficient purity, i.e., 99.85 wt % to 99.90 wt % or higher, without the need to process the benzene through an extraction unit.

The isomerized stream 136 is provided to a deheptanizer column 150, in which a $C_{7-}$ aromatics stream 152 is separated from a $C_{8+}$ aromatics stream 154. Optionally, the isomerization effluent 136 may be passed through a stabilizer column 140 to remove a $C_{5-}$ and light gas stream 142 from a $C_{6+}$ stream 144, which is provided to the deheptanizer column 150. The $C_{8+}$ aromatics stream 154, in which the para-xylene mol % of total xylenes is approximately 24%, is recirculated to the xylenes column 110. Because the inventive process produces benzene with sufficient purity for separation and sale, the $C_{7-}$ aromatics stream 152 may bypass the extraction unit via line 166 and be fed directly to the benzene column 170. A purified benzene stream 172 is removed from the benzene column 170 and may be sold as product. The toluene-containing stream 174 is sent to a toluene column 180 to produce a toluene stream 182 and a heavier aromatics stream 184 that is recycled to the xylenes column 110.

Additional benefits include the requirement for about 20% less catalyst in the isomerization reactor due to the higher WHSV and energy savings due to the lower pressure. Further, because the process achieves high ethylbenzene conversion, less ethylbenzene is recycled through the para-xylene recovery unit, resulting in additional energy savings and enhanced capacity for the para-xylene recovery unit.

The invention will now be more particularly described with reference to the following non-limiting Examples.

EXAMPLE 1

In all the examples provided below, benzene purity is calculated as follows: Benzene purity=(wt % benzene)/(wt % benzene+0.1*wt % n-hexane+0.7*wt % methylcyclopentane+wt % cyclohexane+0.6*(wt % ethylcyclopentane+wt % dimethylcyclopentane)+0.05*wt % methylcyclohexane).

A feed having the composition set forth in Table 1 below was subjected to vapor phase isomerization using a catalyst system such as the system described in U.S. Pat. No. 7,271,118 under differing ethylbenzene conversion (EBC) conditions. The top bed of the catalyst system contained ZSM-5 having a medium crystal size, a silica binder, and approximately 0.03 wt % platinum, was exposed to three selectivation sequences, and had an alpha value of approximately 500. The bottom bed of the catalyst system contained ZSM-5 to having a small crystal size, a silica binder, and approximately 0.01 wt % platinum, and had an alpha value of approximately 108. The WHSV, hydrogen to hydrocarbon ratio, pressure and hydrogen partial pressure was kept constant to analyze the effect of ethylbenzene conversion on the xylenes loss and benzene purity in the effluent. The results are shown in Table 2.

TABLE 1

Example 1 feed composition (in wt %)

| | |
|---|---|
| Benzene | 0.0 |
| Toluene | 0.7 |
| Ethylbenzene | 12.3 |
| Para-xylene | 3.4 |
| Ortho-xylene | 18.3 |
| Meta-xylene | 64.1 |
| $C_9$ Aromatics | 0.0 |
| $C_{10+}$ Aromatics | 0.0 |
| Non-Aromatics | 1.3 |
| Total | 100.0 |

TABLE 2

Example 1 results

| | | | | | |
|---|---|---|---|---|---|
| WHSV ($hr^{-1}$) | 12.0 | 12.0 | 12.0 | 12.0 | 12.0 |
| $H_2$:HC | 1.2 | 1.2 | 1.2 | 1.2 | 1.2 |
| Pressure (psig) | 227.1 | 226.7 | 226.9 | 227.2 | 227.2 |
| $H_2$ PP (psia) | 130.4 | 130.1 | 130.2 | 130.4 | 130.4 |
| EBC (%) | 89.6 | 79.9 | 69.8 | 59.6 | 50.1 |
| Average Reactor Tempearture (° C.) | 389.7 | 374.2 | 363.0 | 353.5 | 345.7 |
| Xylenes Loss (%) | 3.6 | 2.5 | 2.0 | 1.6 | 1.4 |
| PXAE (%) | 102.3 | 101.9 | 101.3 | 100.1 | 98.6 |
| Benzene Purity (wt %) | 99.5 | 99.3 | 99.0 | 98.8 | 98.6 |

The results indicate that, in order to minimize undesirable xylene losses, it is preferable to operate at lower EBC. However, lower EBC means higher recycle in the xylene loop and also lower PX capacity for the adsorption unit. Furthermore, lower EBC also corresponds to the lowest benzene product purity. It should also be noted that regardless of the operating conditions, a benzene product purity sufficient to bypass the extraction unit (i.e., in the range 99.85%-99.90% or higher) is not achieved under these conditions.

EXAMPLE 2

A feed with a composition of that shown in Table 1 was subjected to vapor phase isomerization at different WHSVs, with constant hydrogen to hydrocarbon ratio, pressure and hydrogen partial pressure, to analyze the effect of WHSV on xylenes loss and benzene purity. The results are shown in Table 3.

TABLE 3

Example 2 results

| | | |
|---|---|---|
| WHSV ($hr^{-1}$) | 12.0 | 15.0 |
| $H_2$:HC | 1.2 | 1.2 |
| Pressure (psig) | 226.7 | 227.1 |
| $H_2$ PP (psia) | 130.1 | 129.9 |
| EBC (%) | 79.9 | 81.2 |
| Average Reactor Temperature (° C.) | 374.2 | 384.5 |

TABLE 3-continued

Example 2 results

| | | |
|---|---|---|
| Xylenes Loss (%) | 2.5 | 2.5 |
| PXAE (%) | 101.9 | 102.1 |
| Benzene Purity (wt %) | 99.3 | 99.5 |

Table 3 shows that with higher WHSV, average reactor temperature needs to be to increased to maintain EB conversion to a similar level. The noticeable result is that benzene purity increases from 99.3 wt % to 99.5 wt % as WHSV increases from 12 $hr^{-1}$ to 15 $hr^{-1}$, while EB conversion and xylene losses remain at the same level.

EXAMPLE 3

A feed with a composition of that shown in Table 1 was subjected to vapor phase isomerization at different pressure and hydrogen partial pressure, with constant WHSV and hydrogen to hydrocarbon ratio, to analyze the effect on xylenes loss and benzene purity. The results are shown in Table 4.

TABLE 4

Example 3 results

| | | |
|---|---|---|
| WHSV ($hr^{-1}$) | 15.0 | 15.0 |
| $H_2$:HC | 1.2 | 1.2 |
| Pressure (psig) | 227.1 | 179.6 |
| $H_2$ PP (psia) | 129.9 | 104.4 |
| EBC (%) | 81.2 | 79.8 |
| Average Reactor Temperature (° C.) | 384.5 | 384.6 |
| Xylenes Loss (%) | 2.5 | 2.1 |
| PXAE (%) | 102.1 | 102.0 |
| Benzene Purity (wt %) | 99.5 | 99.85 |

Table 4 shows that benzene purity increases from 99.5 wt % to 99.85 wt %, meaning the isomerization benzene meets benzene product specification and does not need to be re-extracted. Additionally, there is no impact to para-xylene approach to equilibrium (PXAE) and no impact to xylene losses. In fact, xylene losses decrease to 2.1% at lower pressure vs. 2.5% initially.

Catalyst System

Alternatively, or in conjunction with the above described process conditions, a catalyst system is provided to produce benzene in the vapor phase isomerization reaction that does not need to be extracted to achieve sufficient purity to be sold as a product. The catalyst system used in the present process includes a first ethylbenzene conversion catalyst and a second xylene isomerization catalyst. As their names suggest, the first catalyst has the primary function of selectively converting the ethylbenzene in the feedstream, preferably by dealkylation, to benzene and $C_2$ components, while the second catalyst component selectively isomerizes xylenes in the feed. The first catalyst component can, and preferably will, effect some isomerization of the xylenes in the feed.

Each of the first and second catalyst components comprises a molecular sieve and a hydrogenation metal or metal compound.

In one embodiment, the molecular sieve of each of the first and second catalyst components is an intermediate pore size molecular sieve having Constraint Index, before any selectivation, of about 1 to about 12 (e.g., having a pore size less than about 7 Angstroms, such as from about 5 to less than 7 Angstroms). The method by which Constraint Index is determined is described fully in U.S. Pat. No. 4,016,218, incorporated herein by reference for details of the method. Suitable intermediate pore size molecular sieves are those having the structure types MFI, MEL, MTW, TON, MTT, FER, and MFS using the designations adopted by the IUPAC Commission on Zeolite Nomenclature. Conveniently, the molecular sieves are aluminosilicate forms having a silica/alumina molar ratio of at least 12. Examples of intermediate pore size molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780), with ZSM-5 being particularly preferred. The entire contents of the above patents are incorporated by reference herein.

The molecular sieve of the first catalyst component also contains platinum as a hydrogenation metal. In most embodiments, the platinum will be the only hydrogenation metal present in the first catalyst component, but in some embodiments, other hydrogenation metals may also be present in addition to platinum. Suitable additional hydrogenation metals include other Group 8 metals (i.e., Pd, Ir, Rh, Os, Ru, Ni, Co, and Fe), Group 6 metals (i.e., Cr, Mo, W), Group 14 metals (i.e., Sn and Pb), Group 15 metals (i.e., Sb and Bi), and Group 7 metals (i.e., Mn, Tc and rhenium). The amount of the platinum present in the first catalyst component is suitably from about 0.01 to about 1 percent by weight, preferably from about 0.01 to about 0.1 percent by weight, more preferably from about 0.1 to about 0.05 percent by to weight, and ideally about 0.03 percent by weight.

The molecular sieve of the second catalyst component also contains rhenium as a hydrogenation metal. In most embodiments, the rhenium will be the only hydrogenation metal present in the second catalyst component, but in some embodiments, other hydrogenation metals may also be present in addition to rhenium. Suitable additional hydrogenation metals include Group 8 metals (i.e., Pt, Pd, Ir, Rh, Os, Ru, Ni, Co, and Fe), Group 6 metals (i.e., Cr, Mo, and W), Group 14 metals (i.e., Sn and Pb), Group 15 metals (i.e., Sb and Bi), and other Group 7 metals (i.e., Mn and Tc). The amount of the rhenium present in the second catalyst component is suitably from about 0.1 to about 1 percent by weight, preferably from about 0.2 to about 0.8 percent by weight, more preferably from about 0.4 to about 0.6 percent by weight, and ideally about 0.5 percent by weight.

It is to be appreciated that the hydrogenation metal is not necessarily present on the catalyst in the free metal (i.e., zero valent) form, but can also be present as a compound, such as an oxide, hydroxide or sulfide, of the metal. The metal is typically in an oxidized valence state, e.g., when this component is in the form of an oxide or hydroxide. The reduced valence state of the metal may be attained, in situ, prior to or during the course of a reaction, when a reducing agent, such as hydrogen, is included in the feed to the reactor(s).

The hydrogenation metal may be incorporated into the catalyst by methods known in the art, such as ion exchange, impregnation or physical admixture. For example, solutions of appropriate metal salts may be contacted with the remaining catalyst components under conditions sufficient to combine the respective components. The metal containing salt is preferably water soluble. Examples of suitable salts for the incorporation of rhenium in the catalyst components include perrhanate salts, such as ammonium perrhenate. After incorporation of the metal, the catalyst is calcined at a temperature of from about 250° C. to about 500° C.

It may be desirable to formulate either or both of the first and second catalyst components with another material resistant to the temperature and other conditions of the process. Such matrix materials include inorganic oxide materials such as clays, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components can also be used. In addition, the molecular sieve can be composited with a zeolitic matrix material using the method described in International Patent Publication No. WO 96/16004, the entire contents of which are incorporated herein by reference.

The relative proportions of molecular sieve component and inorganic oxide matrix on an anhydrous basis may vary widely with the molecular sieve content ranging from between about 1 to about 99 percent by weight and more usually in the range of about 10 to about 80 percent by weight of the dry composite. Preferably the molecular sieve component and inorganic oxide matrix are present at a ratio of about 80:20 to 60:40, ideally about 65:35.

Selectivation of the either or both of the catalyst components is conveniently achieved by deposition on the surface of the catalyst particles of a layer of coke and/or an oxide, such as silica, which is inert under the process conditions experienced in use.

Where the either or both catalyst components are selectivated with silica, this can be effected by subjecting the catalyst to one or more treatments with an organosilicon compound in a liquid carrier, each treatment being followed by calcination of the treated material in an oxygen-containing atmosphere, e.g., air. Such a multiple selectivation procedure is described in U.S. Pat. No. 5,476,823, the entire contents of which are incorporated herein by reference. Where the catalyst to be silica-selectivated includes a binder, it is preferable to employ a non-acidic binder, such as silica.

The organosilicon compound, which is used to selectivate the first catalyst component may, for example, be a silicone, a siloxane, a silane or mixture thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, to ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane, or silane compound need not be linear, but may be cyclic, for example, hexamethyl cyclotrisiloxane, octamethyl cyclotetrasiloxane, hexaphenyl cyclotrisiloxane, and octaphenyl cyclotetra-siloxane. Mixtures of these compounds may also be used as preselectivating agents, as may silicones with other functional groups.

Typically, the kinetic diameter of the organosilicon compound, that is used to preselectivate the molecular sieve, is larger than the molecular sieve pore diameter, in order to avoid entry of the organosilicon compound into the molecular sieve pores and any concomitant reduction in the internal activity of the molecular sieve.

Suitable organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

The liquid carrier for the organosilicon compound may be an organic compound, such as a linear, branched or cyclic hydrocarbon having 5 or more, especially 7 or more, carbon atoms per molecule, e.g., an alkane, such as heptane, octane, nonane or undecane. The boiling point of the organic compound, e.g., alkane, may be greater than about 70° C. Mixtures of low volatility organic compounds, such as hydrocracker recycle oil, may be employed as carriers. Suitable organic carriers are decane and dodecane.

Following each impregnation with the organosilicon compound, the catalyst is calcined at a ramp rate from about 0.2° C./minute to about 5° C./minute to a temperature greater than 200° C., but below the temperature at which the crystallinity of the molecular sieve is adversely affected. This calcination temperature will generally be below 600° C. and preferably is within the approximate range of 350° C. to 550° C. The duration of heating at the calcination temperature may be from 1 to 24 hours, e.g., from 2 to 6 hours.

The conditions used in a process employing the inventive catalyst are not narrowly defined, but generally will include a temperature of from about 400 to about 1,000° F. (204° C. to 540° C.), a pressure of from about 0 to about 1,000 psig (100 to 7000 kPa), a to weight hourly space velocity (WHSV) of from about 0.5 and about 100 hr$^{-1}$, and a hydrogen, $H_2$, to hydrocarbon, HC, molar ratio of between about 0.1 and about 10. Typical conditions include a temperature of 570° F. to 900° F. (299° C. to 482° C.), a pressure from 100 to 600 psig (696 to 4,238 kPa-a), a weight hourly space velocity (WHSV) from 1 to 50 hr$^{-1}$, and a $H_2$/HC mole ratio from 0.5 to 5. The conditions described above in relation to the inventive process may also be used.

In general, the process is carried out in a fixed bed reactor containing the catalyst system described above. In one embodiment, the first and second components of the catalyst system are located in sequential beds in a single reactor. That is, the component of the catalyst system used in the process of the invention, which is effective for ethylbenzene conversion, forms a first bed, while the other component of the catalyst system, which is effective for xylene isomerization, forms a second bed downstream of the first bed. The feed is suitably cascaded from the first to the second bed without intervening separation of light gases. As an alternative, the first and second beds could be disposed in separate reactors, which, if desired, could be operated at different process conditions. Additional catalyst beds may be provided prior to or after the first and second catalyst components.

After the conversion process, the isomerization product can be treated to isolate para-xylene and/or other desirable xylene(s). Thus, for example, the isomerizate product can be fed to a variety of para-xylene recovery units, such as a crystallizer, a membrane separation unit, or a selective adsorption unit, and thus, the para-xylene may be isolated and recovered. The residual isomerizate can be stripped of products lighter than $C_8$. Products heavier than $C_8$ in the residual isomerizate can be further processed or may be fractionated out. $C_8$ fractions from which para-xylene has been removed can be recycled to the is omerizer.

One result of the process of this invention is to achieve benzene purity at least as high as 99.8%, omitting the need to extract the benzene before preparation for sale. The catalyst system also demonstrated excellent xylene isomerization function with para-xylene approach equilibrium as high as 101.9%.

Another result of the process of this invention is the conversion of a high proportion of the ethylbenzene contained in the mixed xylene feed with minimal xylene loss. For example, ethylbenzene conversion levels of greater than 50 wt % can be accomplished at xylene loss levels of less than 2 wt %. Moreover, the use of rhenium as the hydrogenation metal provides excellent selectivity for ethylene saturation without saturating benzene such to that the benzene fraction after distillation from the final product meets the 99.9 wt % benzene purity specification.

The invention will now be more particularly described with reference to the following non-limiting Example.

EXAMPLE 4

A first catalyst component was prepared by extruding ZSM-5 (at least 1 micron crystals) and an alumina binder in a 65:35 weight ratio into 1/16" diameter cylindrical particles using conventional means. The extrudate was then subjected to a multiple silica-selectivation sequence involving three successive impregnation treatments with 7.8 wt % dimethylphenylmethyl polysiloxane in decane. After each impregnation, the solvent was stripped, and the catalyst was calcinated in $N_2$ and then in air to 538° C. Platinum was then incorporated onto the selectivated catalyst by competitive ion exchange with tetraamine platinum (II) nitrate, followed by drying and air calcination. The final catalyst contained 0.03 wt % of Pt.

A second catalyst component was prepared by extruding ZSM-5B (0.02-0.05 micron crystals) and alumina in a 65:35 weight ratio into 1/16" diameter cylindrical particles using conventional means. The extrudate was then dried, calcined in a nitrogen atmosphere, exchanged with ammonium nitrate, then calcinated in air at 538° C. Rhenium was then incorporated onto the catalyst by incipient wetness impregnation with ammonium perrhenate solution. The final catalyst contained 0.5 wt % of Re.

A feed having the composition set forth in Table 5 below was subjected to vapor phase isomerization using the catalyst system described above. The hydrogen to hydrocarbon ratio, pressure and hydrogen partial pressure were kept constant while two WHSVs were tested to analyze the effect of ethylbenzene conversion on the xylenes loss and benzene purity in the effluent. The results are shown in Table 6.

TABLE 5

| Feed Composition (in wt %) | |
|---|---|
| Benzene | 0.00 |
| Toluene | 0.39 |
| Ethylbenzene | 12.28 |
| Para-xylene | 2.27 |
| Ortho-xylene | 18.83 |
| Meta-xylene | 65.90 |
| $C_9$ Aromatics | 0.03 |
| $C_{10+}$ Aromatics | 0.01 |
| Non-Aromatics | 0.29 |
| Total | 100.00 |

TABLE 6

| Example 4 results | | | | | | |
|---|---|---|---|---|---|---|
| WHSV ($hr^{-1}$) | 12 | 12 | 12 | 15 | 15 | 15 |
| $H_2$:HC | 1.0 | 1.0 | 1.0 | 1.0 | 1.0 | 1.0 |
| Pressure (psig) | 226.9 | 226.9 | 227.3 | 227.4 | 227.5 | 227.4 |
| $H_2$ PP (psia) | 120.8 | 120.8 | 121.0 | 121.0 | 121.1 | 121.0 |
| EBC (%) | 72.7 | 76.0 | 80.8 | 78.7 | 82.1 | 84.7 |
| Average Reactor Temperature (° C.) | 381 | 386 | 395 | 402 | 411 | 418.8 |
| Xylenes Loss (%) | 1.3 | 1.4 | 1.7 | 1.5 | 1.8 | 2.1 |
| PXAE (%) | 99.6 | 100.3 | 101.2 | 100.7 | 101.4 | 101.9 |
| Benzene Purity (wt %) | 99.3 | 99.4 | 99.6 | 99.7 | 99.8 | 99.8 |

Table 6 shows that benzene purity can reach as high as 99.8 wt % at a WHSV of 15 $hr^{-1}$ as the average reactor temperature increased. This benzene purity allows the benzene formed during isomerization to bypass solvent extraction and meet benzene purity standards. Additionally, there is no impact to para-xylene approach to equilibrium (PXAE) and no impact to xylene losses. It is expected that decreasing reactor pressure and/or reducing the hydrogen to hydrocarbon ratio would further increase benzene purity.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing para-xylene from a $C_8$ hydrocarbon mixture comprising ethylbenzene and at least one xylene isomer other than para-xylene, the process comprising:
   (a) contacting the $C_8$ hydrocarbon mixture under ethylbenzene conversion conditions with a first catalyst, comprising a first zeolite and a hydrogenation component comprising platinum, to form an ethylbenzene depleted product, wherein the first zeolite has a constraint index ranging from 1 to 12 and an average crystal size at least 1 micron; and
   (b) contacting the ethylbenzene depleted product under xylene isomerization conditions with a second catalyst comprising a second zeolite and a hydrogenation component comprising rhenium, wherein the second zeolite has a constraint index ranging from 1 to 12 and an average crystal size of about 0.02-0.05 microns.

2. The process of claim 1, wherein the ethylbenzene conversion conditions comprise a temperature from 400 to 1,000° F. (204 to 538° C.), a pressure from 0 to 1,000 psig (100 to 7,000 kPa-a), a weight hourly space velocity (WHSV) from 0.5 to 100 $hr^{-1}$, and a $H_2$/HC mole ratio from 0.1 to 10.

3. The process of claim 1, wherein the xylene isomerization conditions comprise a temperature from 570 to 900° F. (299 to 482° C.), a pressure from 100 to 600 psig (696 to 4,238 kPa-a), a weight hourly space velocity (WHSV) from 1 to 50 $hr^{-1}$, and a $H_2$/HC mole ratio from 0.5 to 5.

4. The process of claim 1, wherein the hydrogenation component of the first catalyst consists essentially of platinum.

5. The process of claim 1, wherein the hydrogenation component of the second catalyst consists essentially of rhenium.

6. The process of claim 1, wherein the first zeolite comprises ZSM-5.

7. The process of claim 1, wherein the second zeolite comprises ZSM-5.

8. The process of claim 1, wherein the first catalyst comprises an alumina binder.

9. The process of claim 1, wherein the second catalyst comprises an alumina binder.

10. A process for producing para-xylene from a $C_8$ hydrocarbon mixture comprising ethylbenzene and at least one xylene isomer other than para-xylene, the process comprising:
    (a) providing a $C_{8+}$ hydrocarbon stream to a para-xylene recovery unit to produce a para-xylene rich stream and a para-xylene depleted stream;
    (b) passing said para-xylene depleted stream to a vapor phase isomerization unit to produce an isomerized stream, wherein said vapor phase isomerization is conducted under conditions of about 175-180 psig, a hydrogen partial pressure of about 100-110 psia, and a WHSV of about 15 $hr^{-1}$;
    (c) providing said isomerized stream to a deheptanizer column to produce a $C_{7-}$ aromatics stream and a $C_{8+}$ aromatics stream;
    (d) recycling said $C_{8+}$ stream back to said para-xylene recovery unit; and
    (e) providing said $C_{7-}$ aromatics stream to a benzene column to recover a benzene stream.

11. The process of claim 10, further comprising separating said $C_{8+}$ hydrocarbon stream to a xylene column prior to step (a) to separate a $C_{9+}$ hydrocarbon stream from the $C_{8+}$ hydrocarbon stream.

12. The process of claim 10, wherein said para-xylene recovery unit comprises an adsorptive separation unit or a crystallization unit.

13. The process of claim 10, wherein said vapor phase isomerization unit contains a catalyst system comprising:
    a first catalyst comprising ZSM-5, a silica binder, and 0.03 wt % platinum; and
    a second catalyst comprising ZSM-5, a silica binder, and 0.01 wt % platinum,
    wherein the first catalyst has an alpha value of at least twice the alpha value of the second catalyst.

* * * * *